(12) United States Patent
Leem (10) Patent No.: US 11,911,202 B2
(45) Date of Patent: Feb. 27, 2024

(54) METHOD AND APPARATUS FOR COMPENSATING SCATTERING OF X-RAY IMAGE

(71) Applicant: VIEWORKS CO., LTD., Anyang-si (KR)

(72) Inventor: Ju Yon Leem, Seongnam-si (KR)

(73) Assignee: VIEWORKS CO., LTD., Anyang-si (KR)

( * ) Notice: Subject to any disclaimer, the term of this patent is extended or adjusted under 35 U.S.C. 154(b) by 155 days.

(21) Appl. No.: 17/680,471

(22) Filed: Feb. 25, 2022

(65) Prior Publication Data
US 2022/0280128 A1 Sep. 8, 2022

(30) Foreign Application Priority Data
Feb. 26, 2021 (KR) .................. 10-2021-0026368

(51) Int. Cl.
*A61B 6/00* (2006.01)
(52) U.S. Cl.
CPC ............ *A61B 6/483* (2013.01); *A61B 6/4208* (2013.01); *A61B 6/5282* (2013.01)
(58) Field of Classification Search
None
See application file for complete search history.

(56) References Cited

U.S. PATENT DOCUMENTS

| 9,633,480 B2 | 4/2017 | Enomoto et al. |
| 2008/0253515 A1 | 10/2008 | Bertram et al. |
| 2016/0296192 A1* | 10/2016 | Noda ..................... G16H 30/40 |

FOREIGN PATENT DOCUMENTS

| EP | 2979636 B1 | 4/2018 |
| KR | 10-1320891 B1 | 10/2013 |
| KR | 20150145633 A | 12/2015 |

* cited by examiner

*Primary Examiner* — Hoon K Song
(74) *Attorney, Agent, or Firm* — Rabin & Berdo, P.C.

(57) ABSTRACT

Provided is a method for compensating scattering of an X-ray image, which includes: (a) receiving an original X-ray image as an input; (b) initializing a primary image into the original X-ray image; (c) estimating a scattered image from the primary image; (d) updating the primary image by using the original X-ray image and the scattered image; (e) judging whether a termination condition is satisfied; (f) iterating steps (c) to (e) above by using the primary image updated through step (d) above into the primary image for step (c) above when the termination condition is not satisfied; and (g) outputting the primary image updated through step (d) above as a scattering compensated image when the termination condition is satisfied.

14 Claims, 9 Drawing Sheets

METHOD AND APPARATUS FOR COMPENSATING SCATTERING OF X-RAY IMAGE

CROSS-REFERENCE TO RELATED APPLICATIONS

This application claims priority to and the benefit of Korean Patent Application No. 10-2021-0026368 filed in the Korean Intellectual Property Office on Feb. 26, 2021, the entire contents of which are incorporated herein by reference.

TECHNICAL FIELD

The present invention relates to a method and an apparatus for compensating scattering of an X-ray image, and more particularly, to a method and an apparatus for compensating scattering of an X-ray image, which can acquire a scattering-compensated image from an original X-ray image without using an anti-scatter grid.

BACKGROUND ART

An X-ray photographing apparatus as an apparatus for acquiring an image by using a feature in which an X-ray is attenuated according to a thickness and an absorption coefficient of an object while passing through the object is widely used in a non-destructive inspection field for inspecting an internal defect of the object in addition to a medical field for diagnosing an inner part of a human body. In the X-ray photographing apparatus, a digital scheme of acquiring the image by using a digital X-ray detector has been replaced with a conventional film scheme in recent years.

Meanwhile, when a radiation ray passes through the object, a phenomenon such as a photoelectric effect, Compton scattering, etc., occurs. By such a phenomenon, a photon may move straight just in a direction in which the photon is incident in a subject (a primary beam) or a progress direction may be changed (a scattered beam). Images created by detecting the primary beam and the scattered beam in a detector are referred to as a primary image and a scattered image, respectively.

The primary beam correctly expresses imaging subject, but in the case of the scattered beam, as a scattering angle increases by Compton scattering which is a main scattering phenomenon, energy loss increases, and as a result, the imaging subject is scattered based on a detection location. In the detector, an image in which the primary image by the primary beam and the scattered image by the scattered beam overlap is acquired. The scattered image blurs the primary image to decrease a contrast of the image, and as a result, a quality of the image deteriorates.

Up to now, the anti-scatter grid has been used in order to remove the scattered beam. The anti-scatter grid as a mechanism in which a material (an absorption unit) having a high radiation ray attenuation coefficient and a material (a transmission unit) having a low radiation ray attenuation coefficient are arranged alternately arranges the transmission unit according to the primary beam direction determined according to a photographing structure to make the primary beam pass and block the scattered beam. One example of the anti-scatter grid is disclosed in Korean Patent Registration No. 10-1320891.

Although it is possible to reduce the scattered beam through the anti-scatter grid, the absorption unit non-selectively reduces the primary beam in addition to the scattered beam. Therefore, an irradiation amount of the X-ray should be increased in order to compensate the resulting signal to noise ratio loss. Moreover, when the primary beam direction is not accurately aligned with the transmission unit, a proper effect may not be shown like a case where an artifact occurs in the image, and as a result, there is a problem in that convenience of a photographing task deteriorates for accurate alignment.

SUMMARY OF THE INVENTION

The present invention has been made in an effort to provide a method and an apparatus for compensating scattering of an X-ray image, which can effectively remove a scattering component from an X-ray image through image processing without using an anti-scatter grid.

An exemplary embodiment of the present invention provides a method for compensating scattering of an X-ray image, which includes: (a) receiving an original X-ray image as an input; (b) initializing a primary image into the original X-ray image; (c) estimating a scattered image from the primary image; (d) updating the primary image by using the original X-ray image and the scattered image; (e) judging whether a termination condition is satisfied; (f) iterating steps (c) to (e) above by using the primary image updated through step (d) above into the primary image for step (c) above when the termination condition is not satisfied; and (g) outputting the primary image updated through step (d) above as a scattering compensated image when the termination condition is satisfied.

In step (d) above, the primary image may be updated according to a difference or a ratio between the original X-ray image, and a sum image between the primary image and the scattered image.

In step (c) above, the scattered image may be estimated by using a scatter kernel defined for each thickness.

Step (c) above may include creating a water equivalent thickness (WET) map from a flat field image and the primary image, and estimating the scattered image by using the WET map and the scatter kernel.

In the creating of the WET map, a first WET map may be created from the flat field image and the primary image, and the first WET map may be converted into the WET map by using a region of interest mask having a value of a pixel corresponding to a direct exposure area of the original X-ray image as 0.

The direct exposure area of the original X-ray image may be an area where the pixel value is larger than a predetermined threshold.

In the creating of the WET map, a first WET map may be created from the flat field image and the primary image, and the first WET map may be converted into the WET map by using a field of view map having a probability value which is to correspond to a field of view according to a collimator as the value of the pixel in the original X-ray image.

In step (e) above, the termination condition may be judged according to a difference or a ratio between the primary image updated through step (d) above and the primary image in step (c) above.

In step (e) above, the termination condition may be judged according to an iteration number of steps (c) to (e) above.

Another exemplary embodiment of the present invention provides an apparatus for compensating scattering of an X-ray image, which includes: an image input unit receiving an original X-ray image as an input; and an image processing unit outputting a scattering compensated image for the original X-ray image, in which the image processing unit initializes a primary image into the original X-ray image, performs a first process of estimating a scattered image from the primary image, a second process of updating the primary image by using the original X-ray image and the scattered image, and a third process of judging whether a termination condition is satisfied, and iteratively performs the first to third processes by using the primary image updated through the second process into the primary image for the first process when the termination condition is not satisfied and outputs the primary image updated through the second process as the scattering compensated image when the termination condition is satisfied.

The image processing unit may update the primary image according to a difference or a ratio between the original X-ray image, and a sum image of the primary image and the scattered image.

The image processing unit may estimate the scattered image by using a scatter kernel defined for each thickness in the first process.

The image processing unit may create a water equivalent thickness (WET) map from a flat field image and the primary image and estimate the scattered image by using the WET map and the scatter kernel, in the first process.

The image processing unit may create a first WET map from the flat field image and the primary image, and convert the first WET map into the WET map by using a region of interest mask having a value of a pixel corresponding to a direct exposure area of the original X-ray image as 0, in the first process.

The direct exposure area of the original X-ray image may be an area where the pixel value is larger than a predetermined threshold.

The image processing unit may create a first WET map from the flat field image and the primary image, and convert the first WET map into the WET map by using a field of view map having a probability value which is to correspond to a field of view according to a collimator as the value of the pixel in the original X-ray image, in the first process.

The termination condition may be judged according to a difference or a ratio between the primary image updated through the second process and the primary image in the first process.

The termination condition may be judged according to an iteration number of the first to third processes.

According to an exemplary embodiment of the present invention, a scattering component can be effectively removed from an X-ray image through image processing without using an anti-scatter grid.

The foregoing summary is illustrative only and is not intended to be in any way limiting. In addition to the illustrative aspects, embodiments, and features described above, further aspects, embodiments, and features will become apparent by reference to the drawings and the following detailed description.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, preferred embodiments of the present invention will be described in detail with reference to drawings. In the following description and the accompanying drawings, the same components represent the same reference numerals, respectively, and as a result, a duplicated description thereof will be omitted. Further, in describing the present invention, a detailed explanation of a known related function or component may be omitted to avoid unnecessarily obscuring the subject matter of the present invention.

Figure 1:
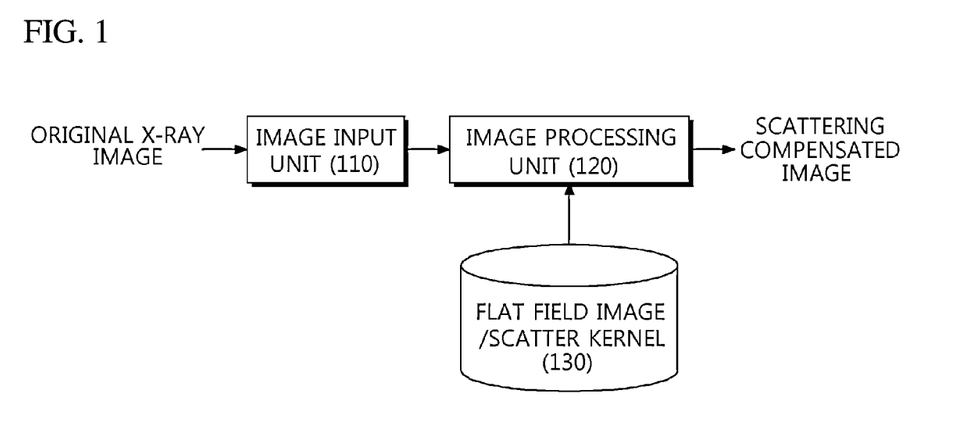
FIG. 1 is a block diagram of an apparatus for compensating scattering of an X-ray image according to an exemplary embodiment of the present invention.

FIG. 1 is a block diagram of an apparatus for compensating scattering of an X-ray image according to an exemplary embodiment of the present invention. The apparatus for compensating scattering of an X-ray image according to the exemplary embodiment may include an image input unit 110, an image processing unit 120, and a database 130.

The image input unit 110 is input with an original X-ray image including a scattering component. The image input unit 110 may be input with the original X-ray image from a detector of an X-ray photographing apparatus. The X-ray photographing apparatus may be various types including a general X-ray photographing apparatus photographing a chest, an arm, a leg, etc., an X-ray photographing apparatus using mammography which is breast photographing technology, an X-ray photographing apparatus using tomography, etc. According to the exemplary embodiment, the original X-ray image may be photographed and stored in advance, and input to the image input unit 110 from an arbitrary storage medium or through a network.

The image processing unit 120 outputs a scattering compensated image from the original X-ray image through image processing. To this end the image processing unit 120 first initializes a primary image into the original X-ray image, and iteratively performs a process of estimating a scattered image from the primary image and a process of updating the primary image by using the original X-ray image and the scattered image to output a finally updated primary image as the scattering compensated image. The image processing unit 120 may output the scattering compensated image to a display apparatus (not illustrated). According to the exemplary embodiment, the image processing unit 120 may output the scattering compensated image to an arbitrary storage medium or may also transmit the scattering compensated image to the outside through a network.

The database 130 stores a flat field image and a scatter kernel. The flat filed image and the scatter kernel may be used in a process in which the image processing unit 120 estimates the scattered image from the primary image.

Figure 2:
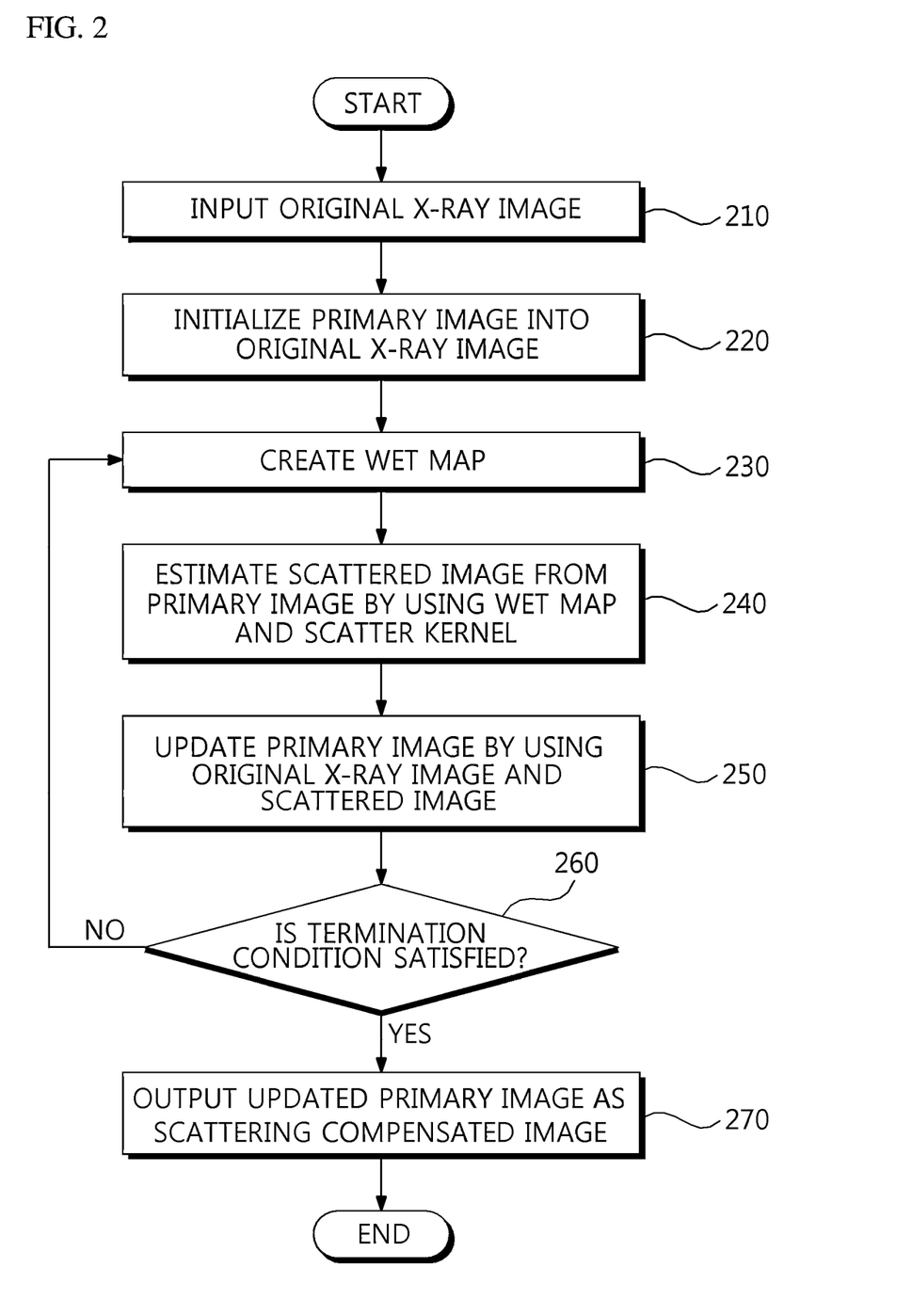
FIG. 2 is a flowchart of a method for compensating scattering of an X-ray image according to an exemplary embodiment of the present invention.

FIG. 2 is a flowchart of a method for compensating scattering of an X-ray image according to an exemplary embodiment of the present invention. Jointly referring to FIG. 2, the apparatus for compensating scattering of an X-ray image according to FIG. 1 will be described in more detail.

In step 210, the image input unit 110 is input with the original X-ray image.

In step 220, the image processing unit 120 first initializes the primary image into the original X-ray image. The image processing unit 120 iterates the process of estimating the scattered image from the primary image and the process of updating the primary image, and since the image processing unit 120 does not first have the primary image for estimating the scattered image, the image processing unit 120 initializes the primary image into the original X-ray image in order to estimate the scattered image.

Hereinafter, the original X-ray image will be represented by I(x,y), the initialized primary image will be represented by $I_p^{(0)}(x,y)$, and an n-th updated (i.e., according to n iterations) primary image will be represented by $I_p^{(n)}(x,y)$. Here, (x,y) represents a coordinate in the image.

Initialization of the primary image may be represented by the following equation.

$$I_p^{(0)}(x,y)=I(x,y) \qquad \text{[Equation 1]}$$

Steps 230 and 240 below correspond to the process in which the image processing unit 120 estimates the scattered image from the primary image.

In step 230, the image processing unit 120 creates a water equivalent thickness (WET) map from the flat field image and the primary image.

Figure 3:
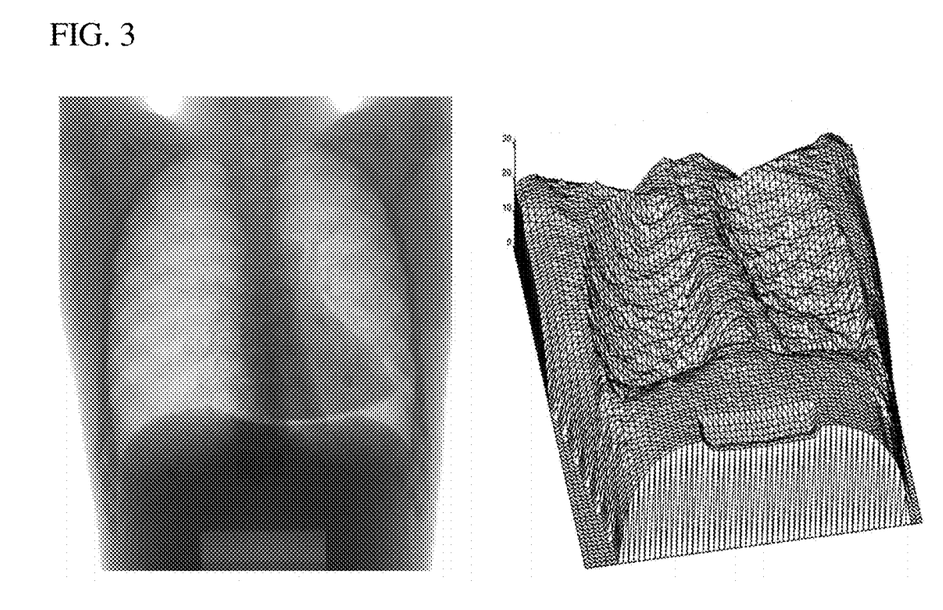
FIG. 3 illustrates one example of an expression of visualizing a WET map in 3 dimension (D).

A water equivalent thickness (WET) is a thickness when a subject is substituted with a water column and the WET map is a map in which the WET is acquired for each pixel of the corresponding image. FIG. 3 illustrates one example of an expression (a right side) of visualizing a WET map in a 3 dimension (D) for any image (a left side).

For the given primary image $I_p^{(n)}(x,y)$, the WET map $\tau(x,y)$ may be approximately acquired by using the following equation according to a Lambert-Beers law.

$$\tau(x,y) \approx \frac{1}{\mu} \cdot \ln\left(\frac{I_0(x,y)}{I_p^{(n)}(x,y)}\right) \qquad \text{[Equation 2]}$$

Figure 4:
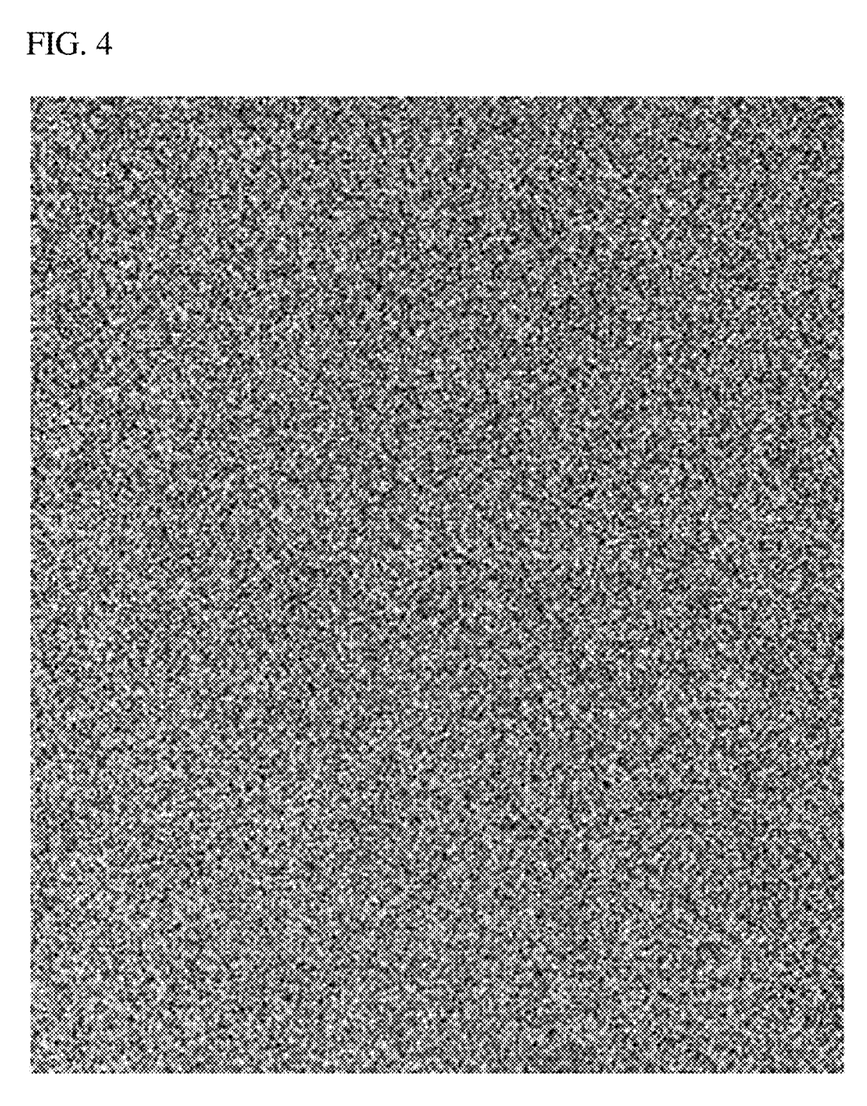
FIG. 4 illustrates one example of a flat field image.

Here, $I_0(x,y)$ as the flat field image is an image photographed without the subject under the same photographing condition (e.g., a tube voltage) as the original X-ray image. FIG. 4 illustrates one example of a flat field image. The flat field image may be photographed in advance for each of various photographing conditions and stored in the database 130, for example, in a form of a look-up table (LUT) for each photographing condition. According to the exemplary embodiment, as the flat field image, an image calculated by using the photographing condition and sensitivity of the detector may also be used. μ is a linear attenuation coefficient of water, and may adopt a value determined according to the tube voltage and also adopt a specific value (e.g., 0.2) in the case of general photographing.

Referring back to FIG. 2, in step 240, the image processing unit 120 estimates the scattered image from the primary image by using the WET map and the scatter kernel.

In general, when the primary image $I_p(x,y)$ is given, the scattered image $I_s(x,y)$ may be estimated through Scatter Kernel Superposition (SKS). When this is expressed by the equation, the corresponding equation is shown below.

$$I_s(x,y) = \iint_D I_p(x',y')h(x-x',y-y')dx'dy' \qquad \text{[Equation 3]}$$

Here, an integral area D is an irradiated area of the detector. h as an impulse response (or also referred to as point spread function (PSF) due to 2D) of a pencil beam input based on (x',y') is referred to as the scatter kernel. As such, the scattered image is expressed as a convolution operation of the primary image and the scatter kernel and this is referred to as Scatter Kernel Superposition (SKS). The original X-ray image I(x,y) acquired by the detector may be expressed as a simple sum of the primary image and the scattered image as in the following equation.

$$I(x,y)=I_s(x,y)+I_p(x,y) \qquad \text{[Equation 4]}$$

Accordingly, when the scatter kernel h is given, the primary image $I_p(x,y)$ and the scattered image $I_s(x,y)$ may be acquired by using Equations 3 and 4.

Figure 5:
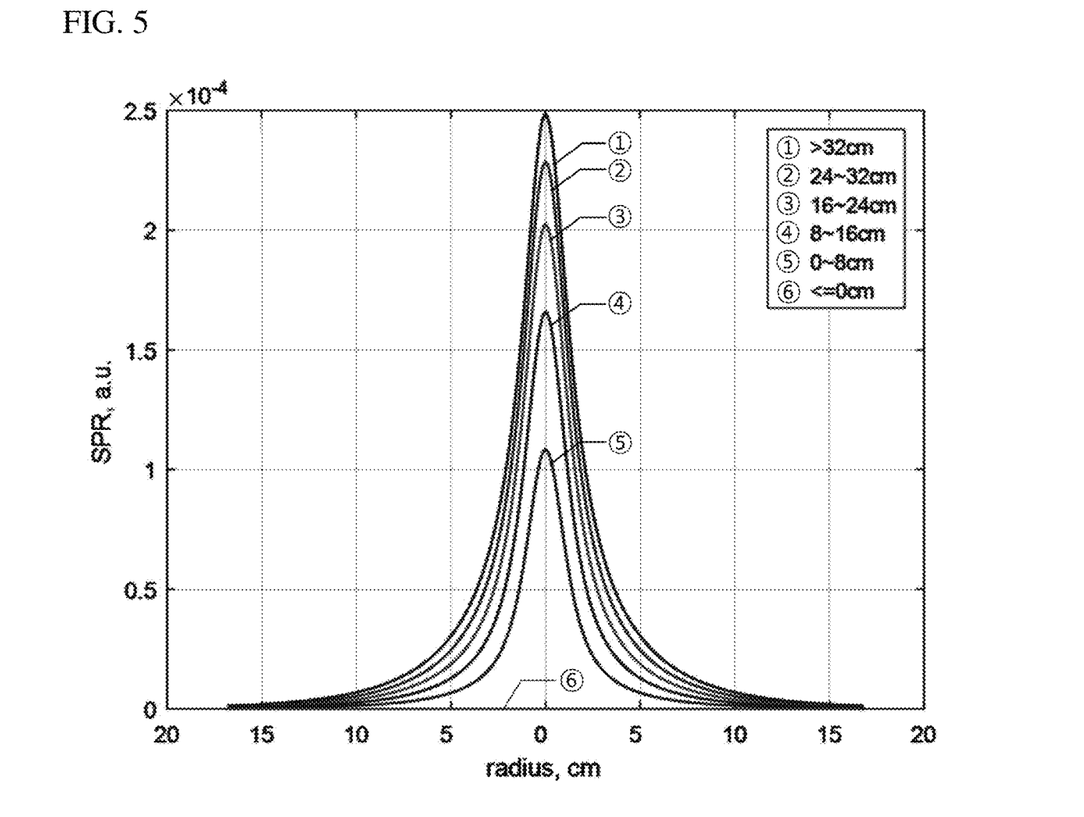
FIG. 5 is a graph of expressing scatter kernels defined for each of various thicknesses in 1D.

In general, when it is assumed that the scatter kernel satisfies an isotropic property, the scatter kernel may be represented by a scatter-to-primary ratio (SPR) which is a strength according to a radius simply without direction information. In this case, since more scattered beams are generated as the object becomes thicker, the scatter kernel is defined differently according to a thickness rather than using a scatter kernel fixed to a predetermined thickness to obtain a more similar result to actuality. FIG. 5 is a graph of expressing scattering kernels defined for each of various thicknesses in 1D.

Further, since more scattered beams are generated as the tube voltage become higher, the scatter kernel may also be defined differently according to the tube voltage. Accordingly, the database 130 may store the scatter kernel in the form of the look-up table for each tube voltage and for each thickness.

For example, the tube voltage may have a range from 60 kVp to 150 kVp as a unit of 1 kVp and the thickness may have a range from 1 cm to 35 cm as a unit of 2 cm. A scatter kernel for a thickness less than 1 cm may prevent scattering by a corresponding pixel by using a zero function. The scatter kernel stored in the database 130 may be created by various methods. For example, the scatter kernel may be measured through an experiment by implementing an actual physical experimental environment, assumed by a mathematical function such as a Gaussian function, etc., or obtained through a Monte Carlo simulation such as EGSnrc, MCNP, GATE, etc., by virtually implementing the experimental environment. Through the methods, the scatter kernel may be approximated by an isotropic 2D low-frequency pass filter.

Since the WET map is obtained through step 230, the scattered image may be estimated by using the WET map and the scatter kernel defined for each thickness in step 240. An equation for estimating the scatter image may be expressed as follows.

$$I_s^{(n)}(x,y) = \sum_i \left( \int\int_D I_p^{(n)}(x', y') R^i(x', y') h^i(x-x', y-y') dx' dy' \right)$$ [Equation 5]

Here, $I_s^{(n)}(x,y)$ represents the scattered image estimated from $I_p^{(n)}(x,y)$ and $h^i$ represents the scatter kernel defined for an i-th thickness interval. $R^i(x,y)$ as a mask for extracting only pixels corresponding to the i-th thickness interval may be expressed as in the following equation.

$$R^i(x,y) = \begin{cases} 1, & t_i \leq \tau^{(n)}(x,y) < t_{i+1} \\ 0, & \text{otherwise} \end{cases}$$ [Equation 6]

Here, $\tau^{(n)}(x,y)$ represents the WET map corresponding to $I_p^{(n)}(x,y)$ and $[t_i, t_{i+1})$ represents the i-th thickness interval.

Figure 6:
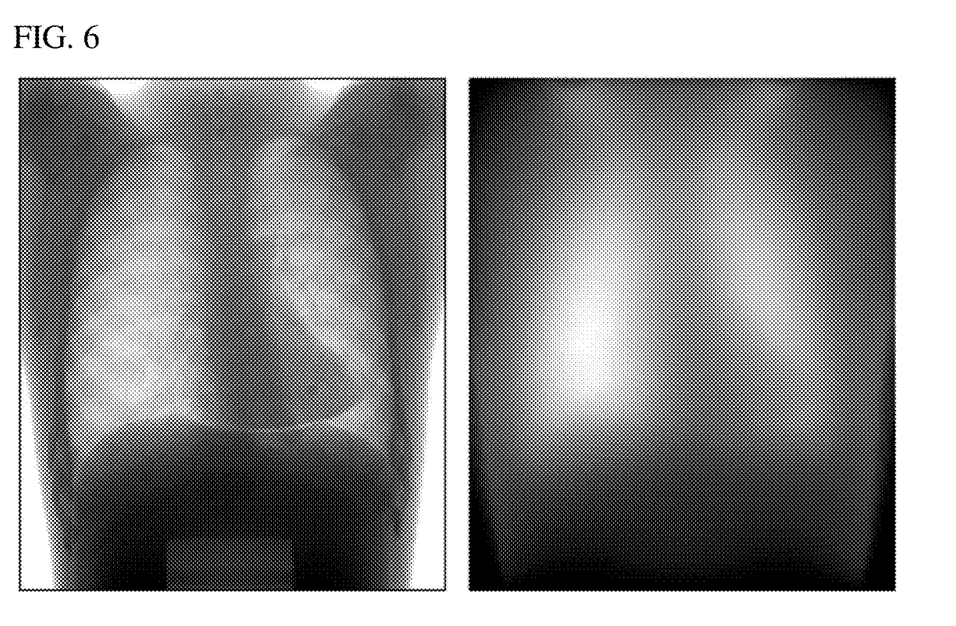
FIG. 6 illustrates one example of a scattered image estimated by using a scatter kernel from a given X-ray image.

FIG. 6 illustrates an example of a scattered image (a right side) estimated by using a scattering kernel from a given X-ray image (a left side).

In step 250, the image processing unit 120 updates the primary image by using the original X-ray image and the scattered image. This process is for modifying the primary image to be close to a real primary image without the scattered beam, and the primary image is initialized into the original X-ray image (step 220), and then the scattered image estimation (steps 230 and 240) and primary image update (step 250) are iterated to obtain a primary image in which scattering in the original X-ray image is compensated.

Since the original X-ray image is expressed by a sum image of the primary image and the scattered image, a difference or a ratio between the original X-ray image, and the sum image of the primary image and the scattered image may become an element of the primary image update.

Accordingly, the primary image may be updated according to the difference between the original X-ray image and the sum image of the primary image and the scattered image based on the primary image in previous iteration (or initialized). This may be expressed as follows.

$$I_p^{(n)}(x,y) = I_p^{(n-1)}(x,y) + \lambda^{(n)} (I(x,y) - (I_p^{(n-1)}(x,y) + I_s^{(n-1)}(x,y)))$$ [Equation 7]

Here, $I_p^{(n)}(x,y)$ represents the primary image updated in current (n-th) iteration, $I_p^{(n-1)}(x,y)$ represents the primary image obtained in previous ((n−1)-th) iteration, and $I_s^{(n-1)}(x,y)$ represents the scattered image estimated from $I_p^{(n-1)}(x,y)$, $\lambda^{(n)}$ as a parameter (or adjusting an update speed) for determining a reflection degree of the difference between the original X-ray image and the sum image may become a specific value (e.g., 0.1) which is irrespective of an iteration number and may also become a value changed (e.g., gradually decreased) according to the iteration number.

The primary image may also be updated according to the ratio between the original X-ray image and the sum image of the primary image and the scattered image based on the primary image in previous iteration (or initialized). This may be expressed as follows.

$$I_p^{(n)}(x,y) = I_p^{(n-1)}(x,y) \frac{I(x,y)}{I_p^{(n-1)}(x,y) + I_s^{(n-1)}(x,y)}$$ [Equation 8]

When the primary image is updated through step 250, the image processing unit 120 judges whether a termination condition is satisfied, i.e., whether the iteration is to be terminated in step 260. If the termination condition is not satisfied, the image processing unit 120 iteratively performs steps 230 to 260 with the primary image updated through step 250.

The termination condition may be judged according to the difference or the ratio between the updated primary image and the previous primary image. When the primary image is updated according to the difference between the original X-ray image and the sum image (Equation 7), for example, when the difference between the updated primary image $I_p^{(n)}(x,y)$ and the previous primary image $I_p^{(n-1)}(x,y)$ is equal to or less than a predetermined threshold, it may be regarded that the termination condition is satisfied. When the primary image is updated according to the ratio between the original X-ray image and the sum image (Equation 8), for example, when the ratio between the updated primary image $I_p^{(n)}(x,y)$ and the previous primary image $I_p^{(n-1)}(x,y)$ is equal to or less than a predetermined threshold, it may be regarded that the termination condition is satisfied. According to the exemplary embodiment, the termination condition may also be judged according to the iteration number irrespective of the difference or the ratio between the original X-ray image and the sum image. According to the exemplary embodiment of the present invention, if the iteration is made approximately 10 times, it may be confirmed that $I_p^{(n)}(x,y)$ converges to a meaningful value. Accordingly, for example, 10 iterations in steps 230 to 250 may be determined as the termination condition.

If the termination condition in step 260 is satisfied, the image processing unit 120 outputs the primary image updated through step 250 as the scattering compensated image in step 270. When it is assumed that the iteration number if the termination condition is satisfied is n, an output image $I_{out}$ becomes an n-th updated primary image as in the following equation.

$$I_{out}(x,y) = I_p^{(n)}(x,y)$$ [Equation 9]

Figure 7:
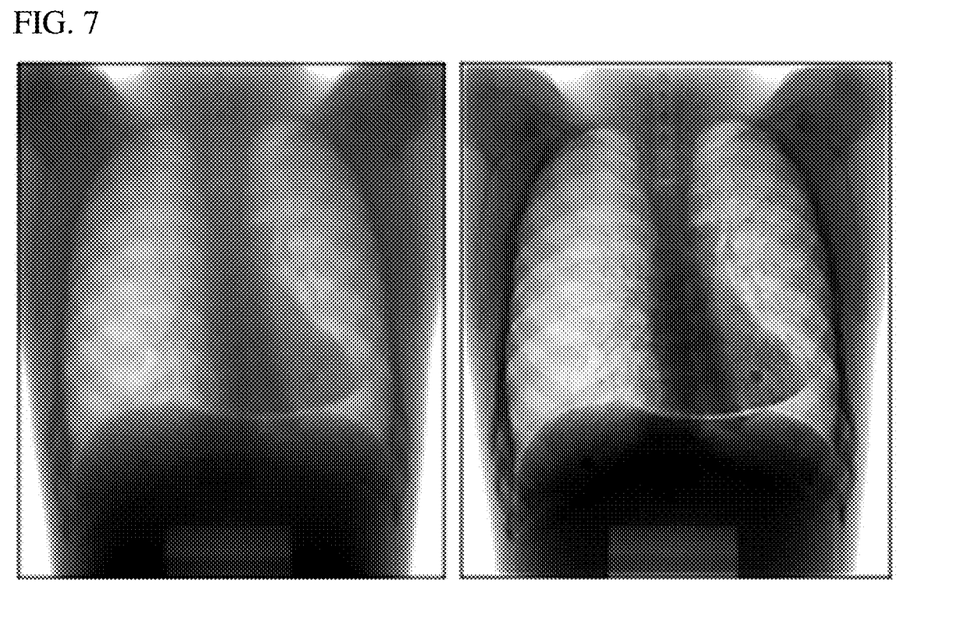
FIG. 7 illustrates an example of a scattering compensated image acquired according to an embodiment of the present invention.

FIG. 7 illustrates an example of a scattering compensated image acquired according to an embodiment of the present invention. Referring to FIG. 7, it may be confirmed that a scattering compensated image (right side) is obtained from the original X-ray image (left side) including the scattering component.

Meanwhile, when the WET map is wrongly calculated in step 230 above, an error may occur during the subsequent scattered image estimation (step 240) and the primary image update (step 250) processes. In particular, when the scattering component is excessively estimated, pixel values of the primary image become negative values and the primary image may not be normally improved even though the iteration is performed during the primary image update process. Hereinafter, modified exemplary embodiments of performing additional processing to the WET map so as to prevent the WET map from being wrongly calculated will be presented.

For convenience, the WET map obtained from the primary image through Equation 2 above will be referred to as a first WET map $\tau'(x,y)$ as in the following equation.

$$\tau'(x,y) \approx \frac{1}{\mu} \cdot \ln\left(\frac{I_0(x,y)}{I_p^{(n)}(x,y)}\right)$$ [Equation 10]

In the original X-ray image, a direct exposure area is an area where the X-ray does not transmit the subject and scattering does not thus occur, and in the case of pixels of a corresponding portion, a value of the WET map should be 0. However, the value of the WET map may be larger than 0 in the corresponding area due to various reasons including noise, etc. Then, not zero function but the scatter kernel is applied to the corresponding area, and the direct exposure area generally has a comparatively high pixel value, and as a result, the quantity of the estimated scattering components also increases. In order to solve this, a part where the pixel value is larger than a predetermined threshold is regarded as the direct exposure area and a region of interest mask having a value of 0 or 1 may be generated for each pixel according to a comparison of the pixel value of the original X-ray image and the threshold. That is, in the region of interest mask, a pixel in which a corresponding pixel value of the original X-ray image is larger than a threshold may have the value of 0 and a pixel in which the corresponding pixel value of the original X-ray image is equal to or smaller than the threshold may have the value of 1. The threshold as a value which becomes a criterion for distinguishing whether the corresponding area is the direct exposure area may be empirically selected by considering the sensitivity of the detector, etc., and for example, in the case of an image of 12 bits (i.e., having a pixel value of 0 to 4095), the threshold may be selected as approximately 2000.

Figure 8:
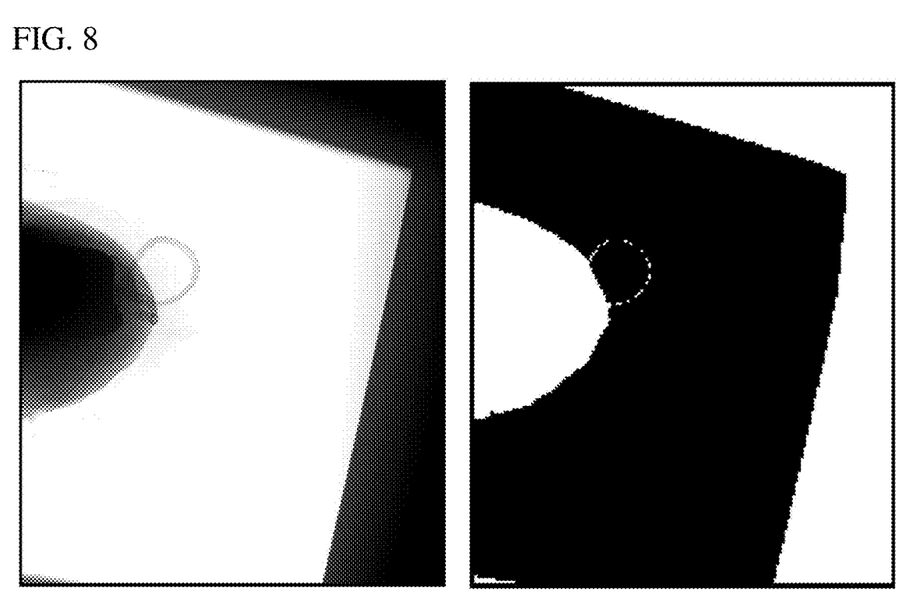
FIG. 8 illustrates an example of a region of interest mask.

FIG. 8 illustrates an example of the region of interest mask, and the left side shows a given image and the right side shows the region of interest mask. Referring to FIG. 8, a part where the pixel value is larger than the threshold in the given image is set to 0 (expressed by black) in the region of interest mask and a part where the pixel value is equal to or smaller than the threshold in the given image is set to 1 (expressed by white) in the region of interest mask.

When the region of interest mask is represented by $M(x,y)$ a first WET map $\tau'(x,y)$ may be converted into a second WET map $\tau''(x,y)$ by using the region of interest mask $M(x,y)$ according to the following equation.

$$\tau''(x,y)=\tau'(x,y)\times M(x,y) \quad \text{[Equation 11]}$$

Here, an operation × represents an elementwise multiplication.

Accordingly, in the second WET map $\tau''(x,y)$, a value of a pixel (corresponding to the direct exposure area) in which the corresponding pixel value of the original X-ray image is larger than the threshold set to 0. The acquired second WET map $\tau''(x,y)$ may be used for estimating the scattered image from the primary image in step 240. The second WET map $\tau''(x,y)$ may allow the scatter kernel to be mapped to zero function in the direct exposure area.

There is a case where an X-ray irradiated area, i.e., a field of view (FOV) is limited by using a collimator upon X-ray photographing. In this case, an outside area (e.g., a black part at an upper right edge in a left image of FIG. 8) of the collimator is calculated as a 'thick' area when generating the WET map. Due to a wrong thickness calculation, when the scattering component is excessively estimated in the outside area of the collimator, a bad influence may be exerted even on the image quality in the FOV. In order to solve this, a so-called FOV map may be generated, which has a probability value in which each pixel is to corresponding to the FOV from the original X-ray image. The FOV map may have a value of 0 or 1 as the probability value.

Figure 9:
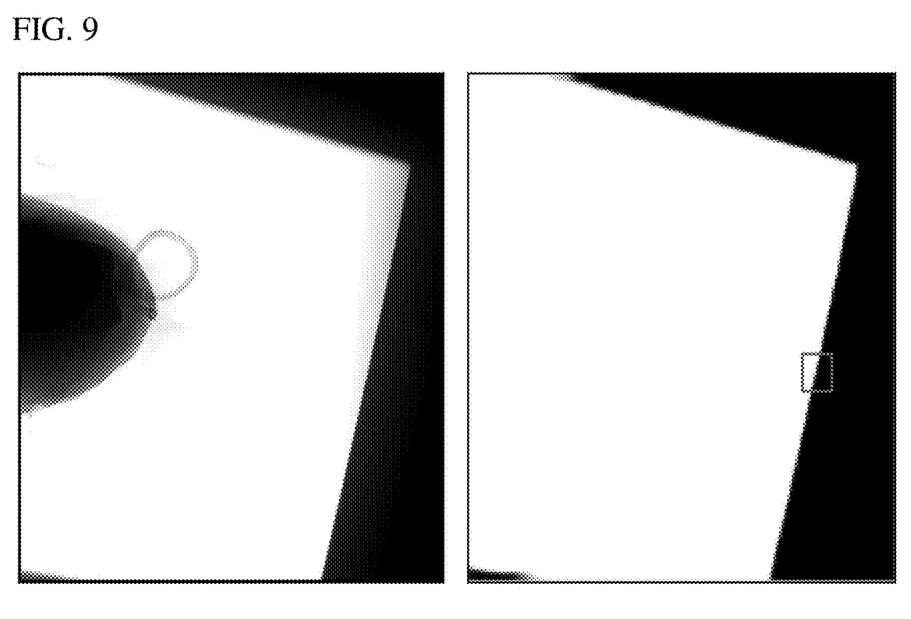
FIG. 9 illustrates an example of a field of view map.
Figure 10:
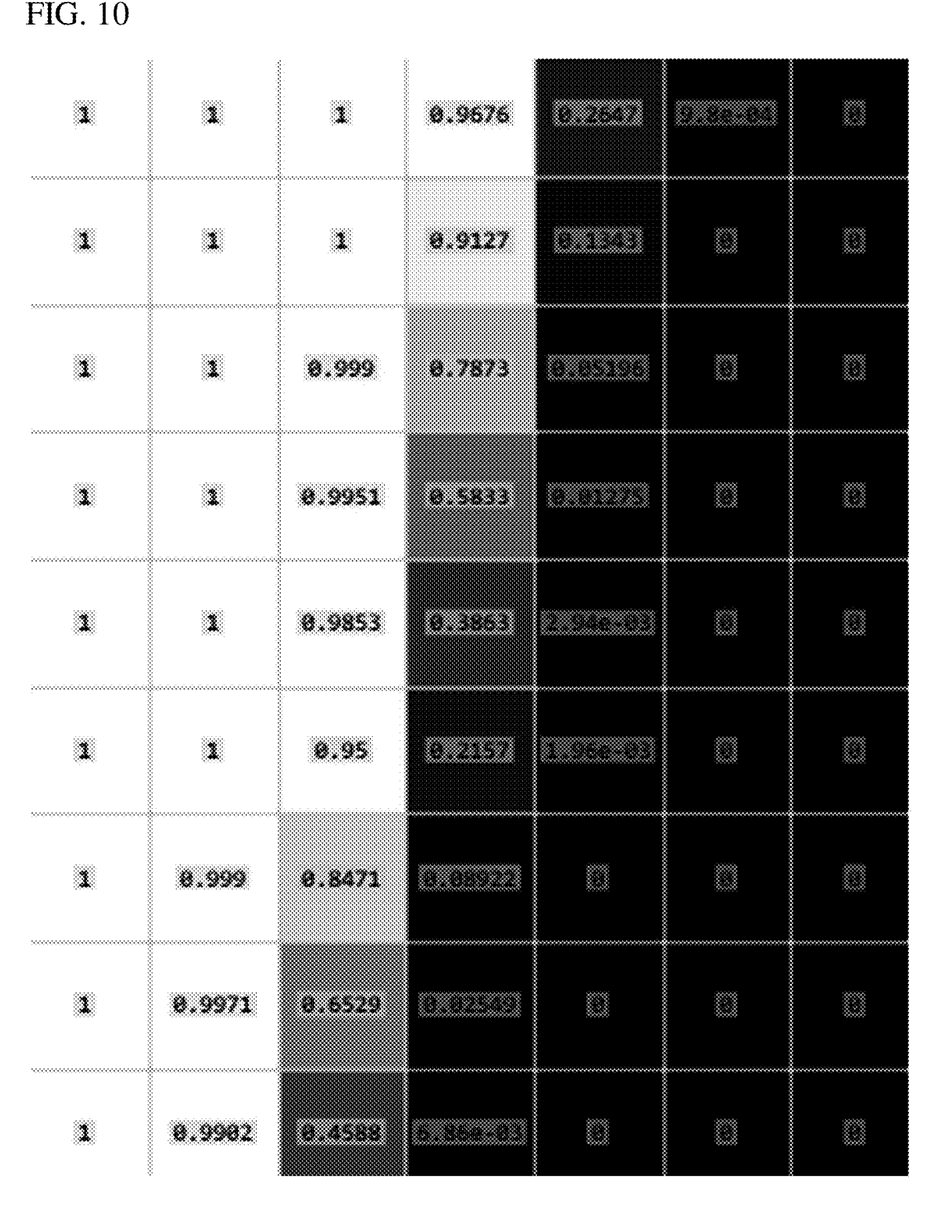
FIG. 10 illustrates enlargement of a part of FIG. 9.

FIG. 9 illustrates an example of the FOV map, and the left side shows the given image and the right side shows the FOV map. FIG. 10 illustrates enlargement of a part (squared) of FIG. 9. Referring to FIGS. 9 and 10, in the FOV map, a part having a high probability to correspond to the FOV has 1 or a value close to 1 and a part having a low probability to correspond to the FOV has 0 or a value close to 0. As illustrated in FIG. 10, the FOV map has a probability value between 0 and 1.

As one example of creating the FOV map, a learning model is created by learning subject images in which the FOV is defined by a machine learning (or deep learning) technique, and the given image is applied to the learning model to derive the FOV map. As another example of the method for creating the FOV map, the FOV map may also be created in a mask form in which an area (e.g., an area where the pixel value is smaller than 25 in the case of the 12-bit image) having a very low pixel value in the given image may has the value of 0 and the remaining area has the value of 1.

When the FOV map is represented by $P_{FOV}(x,y)$, the second WET map $\tau''(x,y)$ may be converted into the WET map $\tau(x,y)$ according to the following equation.

$$\tau(x,y)=\tau''(x,y)\times P_{FOV}(x,y) \quad \text{[Equation 12]}$$

The acquired WET map $\tau(x,y)$ may be used for estimating the scattered image from the primary image in step 240. The WET map $\tau(x,y)$ may allow the scatter kernel to be mapped to the zero function in the direct exposure area and the outside area of the collimator.

Figure 11:
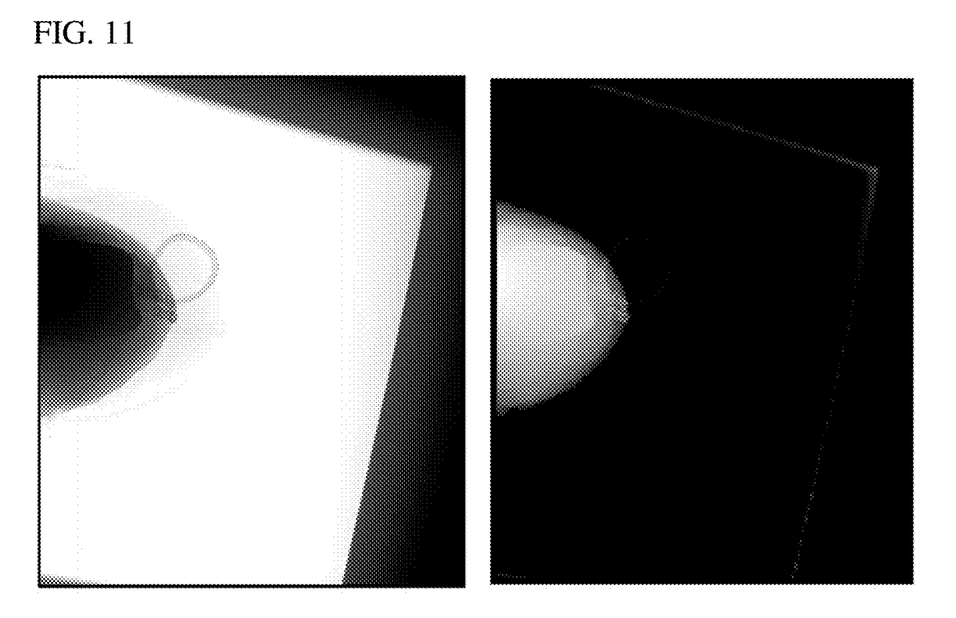
FIG. 11 illustrates an example of a WET map to which the region of interest mask and the FOV map are applied.

FIG. 11 illustrates an example of a WET map to which the region of interest mask and the FOV map are applied. Referring to FIG. 11, it may be confirmed that in the given image (left side), and an area of the WET map (right side) corresponding to a part (direct exposure area) other than the region of interest and the outside area of the collimator has the value of 0 and is marked with black.

FIG. 11 illustrates a WET map to which both the region of interest mask and the FOV map are applied, but according to the exemplary embodiment, a WET map to which only the region of interest mask is applied may also be used and a WET map to which only the FOV map is applied may also be used.

Meanwhile, the apparatus according to the exemplary embodiments of the present invention may include a processor, a memory storing and executing program data, a permanent storage such as a disk drive, a communication port communicating with an external apparatus, a user interface device such as a touch panel, a key, a button, etc., and the like. Methods implemented by a software module or algorithm as computer-readable codes or program commands executable on the processor may be stored in computer-readable recording media. Here, the computer-readable recording media include magnetic storage media (e.g., a read-only memory (ROM), a random-access memory (RAM), a floppy disk, a hard disk, etc.) and optical reading media (e.g., a CD-ROM, a digital versatile disc (DVD), etc.). The computer-readable recording media may be stored and executed as codes which may be distributed in the computer system connected through a network and read by a computer in a distribution method. The media are readable by a computer, stored in the memory executable by the processor.

The exemplary embodiments of the present invention may be represented by functional block components and various processing steps. The functional blocks may be implemented by various numbers of hardware or/and software components executing specific functions. For example, the exemplary embodiments may adopt integrated circuit components including a memory, processing, logic, a look-up table, etc., which may execute various functions by control by one or more microprocessors or by other control devices. Similarly to a case where the component of the present invention may be executed by software programming or software elements, the exemplary embodiment includes a data structure, processes, routines, or various algorithms implemented by a combination of other programming components to be implemented by a programming or scripting language such as C, C++, Java, assembler, etc. Functional aspects may be implemented by an algorithm executed by one or more processors. Further, the exemplary embodiment may adopt related art for electronic environmental setting, signal processing, and/or data processing. Terminologies such as "mechanism", "element", "means", and "component" may be widely used, and are not limited to mechanical and physical components. The terminologies may mean a meaning of a series of routines of software in link with a processor, etc.

Specific executions described in the exemplary embodiment are exemplary embodiments and the scope of the exemplary embodiment is not limited even by any method. For brevity of the specification, descriptions of conventional electronic configurations, control systems, software, and other functional aspects of the systems may be omitted. Further, connection or connection members of lines among components exemplarily represent functions connections and/or physical or circuitry connections and may be represented as various functional connections, physical connections, or circuitry connections which are replaceable or added in an actual device. Further, unless otherwise specified, such as "essential", "important", etc., the connections may not be components particularly required for application of the present invention.

The present disclosure has been described above with reference to preferred embodiments thereof. It is understood to those skilled in the art that the present invention may be implemented as a modified form without departing from an essential characteristic of the present invention. Therefore, the disclosed embodiments should be considered in an illustrative viewpoint rather than a restrictive viewpoint. The scope of the present disclosure is defined by the appended claims rather than by the foregoing description, and all differences within the scope of equivalents thereof should be construed as being included in the present disclosure.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A method for compensating scattering of an X-ray image, the method comprising:
   (a) receiving an original X-ray image as an input;
   (b) initializing a primary image into the original X-ray image;
   (c) estimating a scattered image from the primary image;
   (d) updating the primary image by using the original X-ray image and the scattered image;
   (e) judging whether a termination condition is satisfied;
   (f) iterating steps (c) to (e) above by using the primary image updated through step (d) above into the primary image for step (c) above when the termination condition is not satisfied; and
   (g) outputting the primary image updated through step (d) above as a scattering compensated image when the termination condition is satisfied,
   wherein in step (c) above, the scattered image is estimated by using a scatter kernel defined for each thickness, and
   wherein step (c) above includes
   creating a water equivalent thickness (WET) map from a flat field image and the primary image, and
   estimating the scattered image by using the WET map and the scatter kernel.

2. The method of claim 1, wherein in step (d) above, the primary image is updated according to a difference or a ratio between the original X-ray image, and a sum image of the primary image and the scattered image.

3. The method of claim 1, wherein in the creating of the WET map, a first WET map is created from the flat field image and the primary image, and the first WET map is converted into the WET map by using a region of interest mask having a value of a pixel corresponding to a direct exposure area of the original X-ray image as 0.

4. The method of claim 3, wherein the direct exposure area of the original X-ray image is an area where the pixel value is larger than a predetermined threshold.

5. The method of claim 1, wherein in the creating of the WET map, a first WET map is created from the flat field image and the primary image, and the first WET map is converted into the WET map by using a field of view map having a probability value which is to correspond to a field of view according to a collimator as a value of the pixel in the original X-ray image.

6. The method of claim 1, wherein in step (e) above, the termination condition is judged according to a difference or a ratio between the primary image updated through step (d) above and the primary image in step (c) above.

7. The method of claim 1, wherein in step (e) above, the termination condition is judged according to an iteration number of steps (c) to (e) above.

8. An apparatus for compensating scattering of an X-ray image, the apparatus comprising:
   an image input unit receiving an original X-ray image as an input; and
   an image processing unit outputting a scattering compensated image for the original X-ray image,
   wherein the image processing unit initializes a primary image into the original X-ray image, performs a first process of estimating a scattered image from the primary image, a second process of updating the primary image by using the original X-ray image and the scattered image, and a third process of judging whether a termination condition is satisfied, and iteratively performs the first to third processes by using the primary image updated through the second process into the primary image for the first process when the termination condition is not satisfied and outputs the primary image updated through the second process as the scattering compensated image when the termination condition is satisfied, wherein the image processing unit estimates the scattered image by using a scatter kernel defined for each thickness in the first process, and wherein the image processing unit creates a water equivalent thickness (WET) map from a flat field image and the primary image and estimates the scattered image by using the WET map and the scatter kernel, in the first process.

9. The apparatus of claim 8, wherein the image processing unit updates the primary image according to a difference or a ratio between the original X-ray image, and a sum image of the primary image and the scattered image.

10. The apparatus of claim 8, wherein the image processing unit creates a first WET map from the flat field image and the primary image, and converts the first WET map into the WET map by using a region of interest mask having a value of a pixel corresponding to a direct exposure area of the original X-ray image as 0, in the first process.

11. The apparatus of claim 10, wherein the direct exposure area of the original X-ray image is an area where the pixel value is larger than a predetermined threshold.

12. The apparatus of claim 8, wherein the image processing unit creates a first WET map from the flat field image and the primary image, and converts the first WET map into the WET map by using a field of view map having a probability value which is to correspond to a field of view according to a collimator as a value of the pixel in the original X-ray image, in the first process.

13. The apparatus of claim 8, wherein the termination condition is judged according to a difference or a ratio between the primary image updated through the second process and the primary image in the first process.

14. The apparatus of claim 8, wherein the termination condition is judged according to an iteration number of the first to third processes.

* * * * *